US009392988B2

(12) United States Patent
Kobayashi (10) Patent No.: US 9,392,988 B2
(45) Date of Patent: Jul. 19, 2016

(54) X-RAY IMAGING APPARATUS

(71) Applicant: CANON KABUSHIKI KAISHA, Tokyo (JP)

(72) Inventor: Tsuyoshi Kobayashi, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 328 days.

(21) Appl. No.: 13/709,947

(22) Filed: Dec. 10, 2012

(65) Prior Publication Data

US 2013/0148785 A1 Jun. 13, 2013

(30) Foreign Application Priority Data

Dec. 13, 2011 (JP) ................................. 2011-272160

(51) Int. Cl.
*H05G 1/64* (2006.01)
*A61B 6/00* (2006.01)
*G01T 1/24* (2006.01)

(52) U.S. Cl.
CPC ...... *A61B 6/54* (2013.01); *G01T 1/24* (2013.01); *A61B 6/4233* (2013.01)

(58) Field of Classification Search
None
See application file for complete search history.

(56) References Cited

U.S. PATENT DOCUMENTS

| 3,776,722 | A * | 12/1973 | Cantarano | G03G 15/344 399/130 |
| 5,407,768 | A * | 4/1995 | Akiyama | G03G 5/08221 430/65 |
| 6,457,861 | B1 * | 10/2002 | Petrick | A61B 6/032 378/207 |
| 6,497,511 | B1 * | 12/2002 | Schmitt | H04N 5/325 348/E5.081 |
| 7,550,733 | B2 * | 6/2009 | Endo | A61B 6/4488 250/370.09 |
| 7,659,518 | B2 * | 2/2010 | Adachi | A61B 6/4233 250/370.09 |
| 7,750,309 | B2 * | 7/2010 | Endo | A61B 6/4488 250/370.09 |
| 7,915,589 | B2 * | 3/2011 | Takenaka | H04N 5/217 250/252.1 |
| 8,232,529 | B2 * | 7/2012 | Takenaka | H04N 5/217 250/366 |
| 8,809,796 | B2 * | 8/2014 | Jung | G01T 1/247 250/370.08 |

(Continued)

FOREIGN PATENT DOCUMENTS

JP 2000-111649 A 4/2000
JP 2002199278 A * 7/2002

(Continued)

*Primary Examiner* — Andrew Smyth
(74) *Attorney, Agent, or Firm* — Canon USA Inc., IP Division (57) ABSTRACT

An X-ray imaging apparatus that performs X-ray radiographing by detecting X-rays that have transmitted through an object with an X-ray sensor includes an acquisition unit configured to acquire a first predetermined time based on operational information of the X-ray sensor, and a control unit configured to alter a drive of the X-ray sensor based on whether the first predetermined time has elapsed after bias voltage is applied on the X-ray sensor after X-ray radiographing is performed by the X-ray sensor.

13 Claims, 7 Drawing Sheets

(56) References Cited

U.S. PATENT DOCUMENTS

| | | | | |
|---|---|---|---|---|
| 2003/0186178 A1* | 10/2003 | Gibson | | G03C 7/3005 430/551 |
| 2004/0252874 A1* | 12/2004 | Yamazaki | | H04N 5/32 382/132 |
| 2005/0100806 A1* | 5/2005 | Hongo | | C09B 7/0022 430/78 |
| 2008/0011958 A1* | 1/2008 | Endo | | A61B 6/4488 250/370.08 |
| 2008/0075349 A1* | 3/2008 | Ritter | | G03B 42/02 382/132 |
| 2008/0112533 A1* | 5/2008 | Ogawa | | G03G 21/08 378/28 |
| 2008/0131704 A1* | 6/2008 | Mizuno | | B32B 27/36 428/423.1 |
| 2008/0226031 A1* | 9/2008 | Yokoyama | | A61B 6/585 378/98.7 |
| 2008/0246065 A1* | 10/2008 | Takenaka | | H04N 5/217 257/292 |
| 2009/0224163 A1* | 9/2009 | Endo | | A61B 6/4488 250/370.09 |
| 2010/0020933 A1* | 1/2010 | Topfer | | G06T 5/50 378/98.11 |
| 2011/0121183 A1* | 5/2011 | Takenaka | | H04N 5/217 250/361 R |
| 2012/0033110 A1* | 2/2012 | Tanabe | | A61B 6/585 348/244 |
| 2012/0126132 A1* | 5/2012 | Kimura | | H04N 5/32 250/370.09 |
| 2012/0138808 A1* | 6/2012 | Jung | | G01T 1/247 250/370.09 |
| 2012/0161017 A1* | 6/2012 | Kimura | | H04N 5/32 250/370.09 |
| 2013/0003912 A1* | 1/2013 | De Man | | A61B 6/032 378/5 |
| 2013/0108009 A1* | 5/2013 | Kojima | | A61B 6/032 378/7 |
| 2013/0196872 A1* | 8/2013 | Low | | G01N 33/54353 506/9 |

FOREIGN PATENT DOCUMENTS

| | | | |
|---|---|---|---|
| JP | 2005-028113 A | | 2/2005 |
| JP | 2007181183 A | * | 7/2007 |
| JP | 2008-252424 A | | 10/2008 |
| JP | 2008-264528 A | | 11/2008 |
| JP | 2009028559 A | * | 2/2009 |
| JP | 2010-131223 A | | 6/2010 |
| JP | 2010-253263 A | | 11/2010 |

* cited by examiner

SENSOR OPERATING TEMPERATURE T

FIG. 6B

SENSOR OPERATING TEMPERATURE T

X-RAY IMAGING APPARATUS

BACKGROUND OF THE INVENTION

1. Field of the Invention

The present invention relates to an X-ray imaging apparatus that performs radiographing using X-rays that have transmitted through an object.

2. Description of the Related Art

In recent years, in the medical fields, in place of an analog X-ray imaging apparatus using a film for conventional X-ray diagnosis, a digital X-ray imaging apparatus using a flat panel detector in which pixels composed of semiconductor devices for converting X-rays into electric signals are disposed in a two-dimensional matrix pattern is in widespread use.

In such a digital X-ray imaging apparatus, information of X-rays that have passed through an object is stored in pixels as electric charges. Thereafter, the digital X-ray imaging apparatus performs transfer operation, and reads out the information as voltage, and subsequently performs A/D conversion to acquire digital image information. However, in the electric charge transfer operation of the pixels, it is known that electric charges cannot be all discharged, and residual electric charge appears. Further, accumulation of electric charges in the pixels may alter characteristics of the semiconductor devices and thus may lower their sensitivities.

It is known that, due to these phenomena, when the digital X-ray imaging apparatus is used, a portion of radiographic information of the previous radiographic image appears as an image lag at the time of the next radiographing operation.

Since signals which are not actually present in clinical images will be output as an artifact resulting from such an image lag, it has become a problem in terms of diagnosis. In particular, the kind of image lag generated by change of characteristics of the elements caused by the latter X-ray irradiation, and by degradation of sensitivity includes a component which does not fully decay even in a minute or so, and continues to give influence on diagnosis images for a long period of time. As a result, they have caused impairing of clinical values of the digital X-ray imaging apparatus.

In the present invention, of the image lags of the X-ray imaging apparatus, the one resulting from a large time constant of the above-described decay is handled, which is simply referred to as an image lag.

In order to inhibit such an image lag, a technique for erasing the image lag by shifting to a state where power supply to the semiconductor devices is temporarily stopped each time radiography ends (see, for example, Japanese Patent Application Laid-Open No. 2002-199278) is known. Further, there is known a technique for stabilizing sensitivity and inhibiting generation of the image lag by installing a separate light source unit, and irradiating whole surface of a detector with light rays (see, for example, Japanese Patent Application Laid-Open No. 2007-181183).

However, the above-described conventional technique has a problem. That is, in the technique discussed in Japanese Patent Application Laid-Open No. 2002-199278, although the image lag inhibiting effect is high, a time that elapses before the next radiography becomes possible (hereinafter, referred to as radiography cycle time) will becomes longer. Further, in the technique discussed in Japanese Patent Application Laid-Open No. 2007-181183, sensors will become larger in size, heavier in weight, and higher in cost.

SUMMARY OF THE INVENTION

The present invention is directed to providing an X-ray imaging apparatus capable of performing radiographing which inhibits an image lag, while preventing increase in size or increase in weight of a radiographing unit, and prolongation of an radiography cycle time.

According to the present invention, an X-ray imaging apparatus that performs radiographing by detecting X-rays that have transmitted through an object with an X-ray sensor, includes an acquisition unit configured to acquire a first predetermined time based on operational information of the X-ray sensor, and a control unit configured to alter a drive of the X-ray sensor based on whether the first predetermined time has elapsed after a bias voltage is applied on the X-ray sensor after X-ray radiographing is performed by the X-ray sensor.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Hereinbelow, feasible exemplary embodiments according to the present invention will be described in detail referring to the accompanying drawings.

Figure 1:
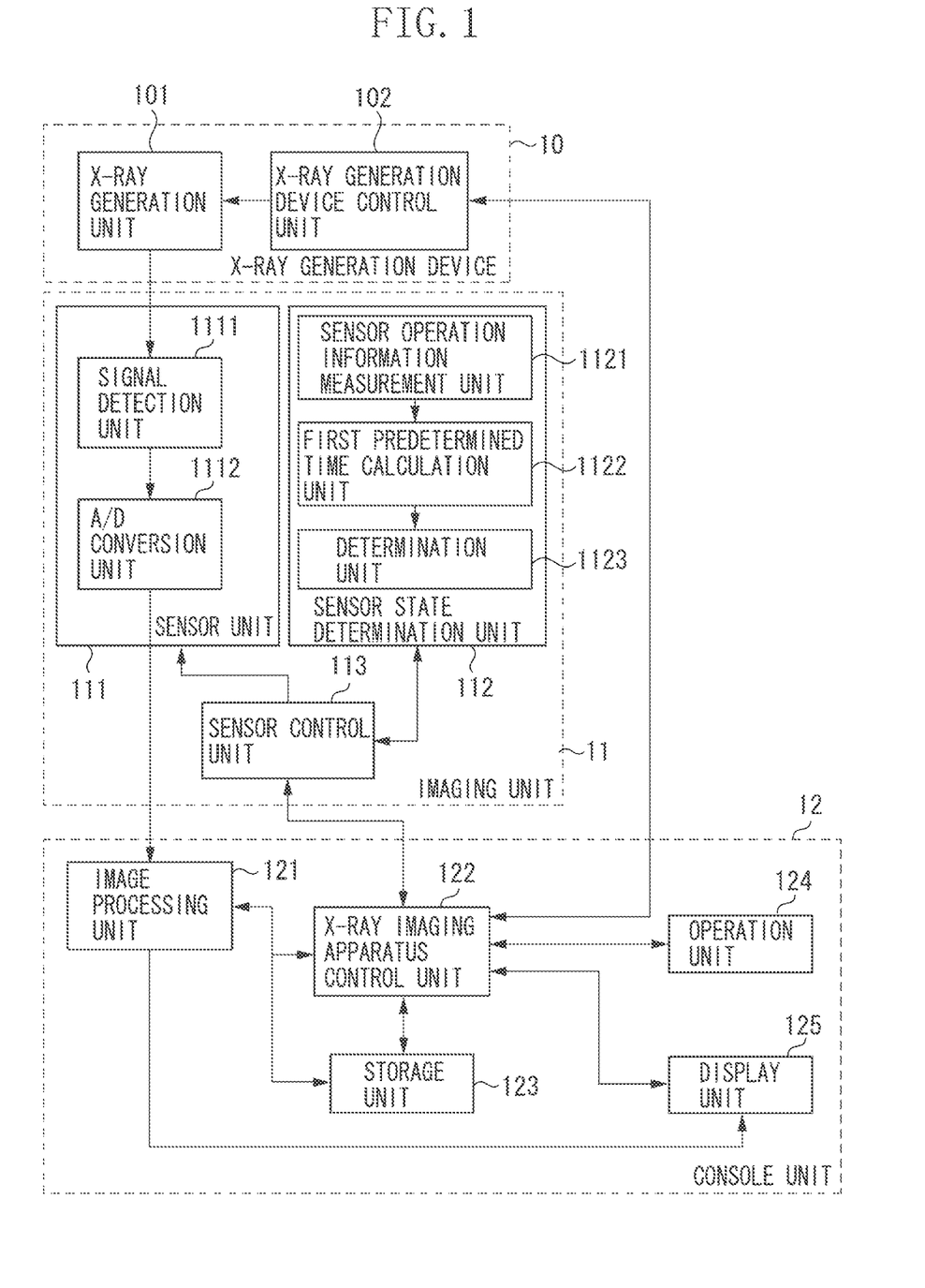
FIG. 1 is a block diagram illustrating a configuration of an X-ray imaging apparatus according to a first exemplary embodiment.

Components and respective functions of the X-ray imaging apparatus according to the first exemplary embodiment will be described. FIG. 1 is a block diagram illustrating an outline configuration of the X-ray imaging apparatus according to the present exemplary embodiment.

First, an outline of the apparatus will be described with reference to FIG. 1. As illustrated in FIG. 1, the X-ray imaging apparatus according to the first exemplary embodiment includes an X-ray generation device 10, a radiographing unit 11, and a console unit 12.

The X-ray generation device 10 includes an X-ray generation unit 101 and an X-ray generation device control unit 102. The X-ray generation device control unit 102 adjusts X-ray irradiation conditions such as tube voltages and tube currents according to a target value specified by an operator, and controls X-ray irradiation by the X-ray generation unit 101.

The radiographing unit 11 includes an X-ray sensor unit 111, a sensor state determination unit 112, and a sensor operation control unit 113. The X-ray sensor unit 111 includes a signal detection unit 1111 and an analog-to-digital (A/D) conversion unit 1112, and converts information of the X-rays which have transmitted through an object into digital image signals. The sensor state determination unit 112 includes a sensor operation information measurement unit 1121, a first predetermined time calculation unit 1122, and a determination unit 1123, and performs measurements of operational information of the X-ray sensor unit 111 and determination of state of the X-ray sensor unit 111.

The sensor operation control unit 113 is electrically connected to the X-ray sensor unit 111, the sensor state determination unit 112, and the X-ray imaging apparatus operation control unit 122, and performs control of operation of the radiographing unit 11 in response to an operation of the operator, or control of drive of the X-ray sensor unit 111 corresponding to a state of the X-ray sensor unit 111.

The console unit 12 includes an image processing unit 121, and the X-ray imaging apparatus control unit 122, a storage unit 123, an operation unit 124 and a display unit 125. Digital image data acquired by the radiographing unit 11 is input into the image processing unit 121, which performs image processing for enhancing diagnosis values.

The X-ray imaging apparatus control unit 122 controls all operations of the X-ray generation device unit 10, the radiographing unit 11, and the console unit 12. The operator can perform operation job of the entire X-ray imaging apparatus at the operation unit 124, and can reflect an operation intended by the operator via the electrically connected X-ray imaging apparatus control unit 122. The image data which has been processed by the image processing unit 121 is stored into the storage unit 123, and is displayed on the display unit 125 in a timely manner, in response to the operation of the operator.

Next, detailed configuration and operation of the radiographing unit 11 will be described.

The signal detection unit 1111 is configured to include a wavelength conversion member that wavelength-converts irradiated X-rays into visible light rays, and a substrate that outputs an electric signal according to the visible light rays. The above-described substrate has a structure in which pixels composed of photoelectric conversion elements are arrayed on a two-dimensional plane of the substrate. As a wavelength conversion member, for example, CsI:TI or Gd2O2S:Tb or the like is suitably used.

According to the present exemplary embodiment, in a case where the X-ray imaging apparatus performs radiographing operation, the signal detection unit 1111 converts information of the X-rays which have passed through an object into visible light rays by the wavelength conversion member, and electrically charges the pixels. Thereafter, the signal detection unit 1111 reads electric charge signals accumulated in individual pixels as voltage information, and generates a detection signal having a level according to an irradiation dose of the X-rays. Subsequently, in an A/D conversion unit 1112, the detection signal (analog signal) generated by the signal detection unit 1111 is converted into a digital signal.

Figure 2:
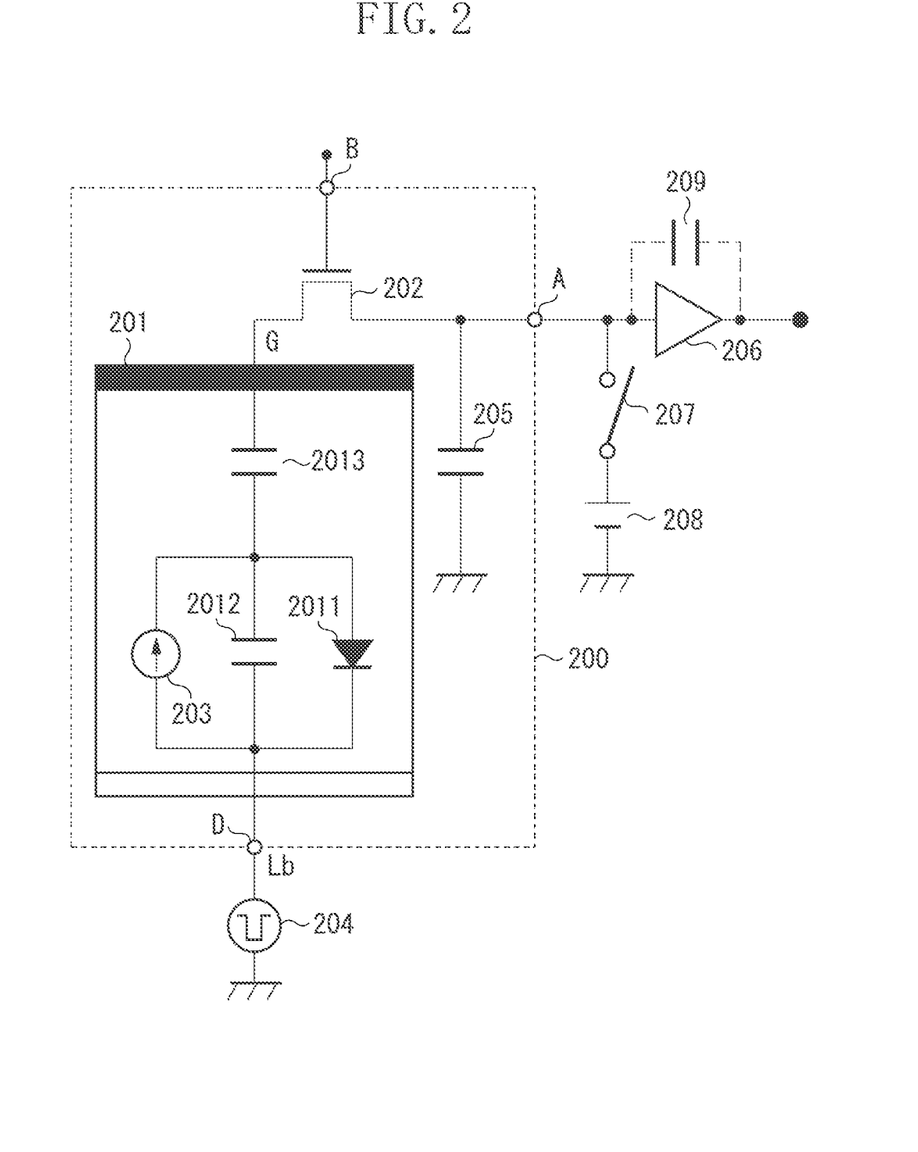
FIG. 2 is a diagram illustrating an example of equivalent circuit on a component basis of a signal detection unit according to the first exemplary embodiment.

FIG. 2 illustrates an example of an equivalent circuit on a component basis of the signal detection unit 1111. Hereinbelow, configurations and operations of the signal detection unit 1111 will be described with reference to FIG. 2. In FIG. 2, a number of pixels is one for convenience of descriptions, but in the present exemplary embodiment, the number of pixels is not limited to one and may be two or more. The number of pixels is appropriately determined as the need arises.

First, circuit configuration will be described. One pixel includes a light detection portion 201 arranged on a glass substrate 200 and a switching thin-film transistor (TFT) 202 that controls accumulation and reading of electric charges. These are generally formed of amorphous silicon on the glass substrate.

The light detection portion 201 further includes a parallel circuit of a reset diode 2011 and the capacitor 2012 and a capacitor 2013 connected in series with the capacitor 2012.

Further, electric charges generated by the photoelectric effect are described as a constant current source 203. The capacitor 2012 may be a parasitic capacitance of the reset diode 2011, or may be an additional capacitor that improves a dynamic range of the reset diode 2011. A common bias electrode of the light detection portion 201 is connected to a bias power source 204 via a bias wiring Lb. An electrode on the switching TFT 202 side of the light detection portion 201 is connected to a capacitor 205 and a preamplifier 206 for electric charge reading via the switching TFT 202. Input of the preamplifier 206 is also connected to the earth via a reset switch 207 and a signal line bias power source 208. Next, a drive performed when reading the signals of one pixel will be described in detail. Hereinafter, a series of operations for altering at predetermined timing, voltages to be applied to the elements that constitute the signal detection unit 1111 or operation of switches, is referred to as a drive.

When a drive of the radiographing unit 11 is started, energization of the signal detection unit 1111 is started, and a bias voltage is applied on the elements by the bias power source 204. Next, the switching TFT 202 and the reset switch 207 are temporarily turned on, and a potential at D is lowered by operating the bias power source 204. The capacitors 2012 and 2013 are reset by the reset diode. After operating the bias power source 204 to raise the potential at D, the switching TFT 202 and the reset switch 207 are sequentially turned off. By performing irradiation of the X-rays at that timing, the X-rays which have transmitted through the object are converted into visible light image by the wavelength conversion member, and electric charges are stored in the capacitor 2012 and the capacitor 2013.

Next, the switching TFT 202 is turned on to connect the capacitor 2012 and the capacitor 205. Accordingly, information of the capacitor 2013 is also transmitted to the capacitor 205. By amplification of voltages of accumulated electric charges of the capacitor 205 with the preamplifier 206, or with a capacitor 209 indicated with a dotted line, signals are converted from electric charge information into voltage information and are output to the outside. Depending on a state of the elements, after a series of signal reading drive has been finished, application of the bias voltage on the elements by the bias power source 204 may be stopped, and a drive for dropping all potentials at A and B and D to the earth (hereinafter, referred to as sleep drive) may be performed.

By performing a sleep drive for each radiographing operation, generation of the image lags can be inhibited, but a time that elapses before the next radiographing becomes possible (hereinafter, referred to as radiography cycle time) will be prolonged.

The above drive uses a metal-insulator-silicon (MIS)-type photoelectric conversion element made of amorphous silicon as a chief material. However, the chief material is not limited to this, and PIN-type photodiode or the like may be used. Further, in the present exemplary embodiment, an indirect method for providing a wavelength conversion member, and converting the visible light rays which have been wavelength-converted from the X-ray into electric signals is used. However, the present exemplary embodiment is not limited to this. For example, in the X-ray imaging apparatus composed of a light-receiving portion made of, amorphous Se or PbI2, and an amorphous silicon TFT, a direct method for directly converting the X-rays into electric signals on the substrate without using the wavelength conversion member may be used.

The X-ray sensor unit 111 as described above has a problem of an image lag generated by change of the characteristics of the elements according to an elapsed time after the bias voltage is applied to the elements, or under the influence of X-rays irradiated on the apparatus. Hereinbelow, the results of study on characteristic change of the radiation imaging apparatus will be described. The followings will describe examples of verification experiments on characteristic changes of the X-ray sensor unit 111 with reference to FIGS. 3A to 3C.

Figure 3A:
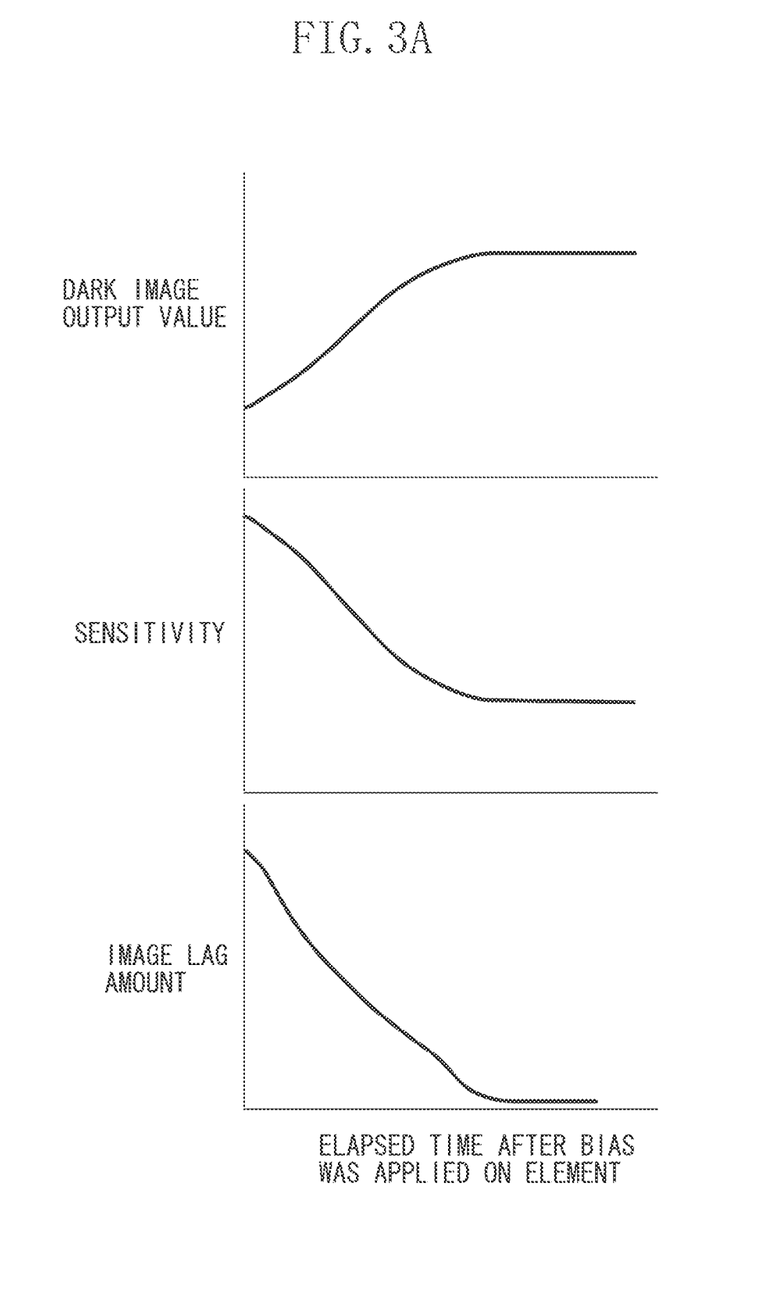
FIGS. 3A, 3B, and 3C illustrate examples of experimental results representing temporal characteristics of output values of a sensor unit of the X-ray imaging apparatus in the first exemplary embodiment.

FIG. 3A is an example of a result of an experiment for observing characteristics of the X-ray sensor unit 111 when operation is continued without performing X-ray irradiation, after the bias voltage has been applied on the elements. In this case, a relationship between a time during which the operation is continued without performing the X-ray irradiation by applying the bias voltage on the elements, and the characteristics of the X-ray sensor unit 111 has been observed.

As an example of the characteristics of the X-ray sensor unit 111, an output value of an image on which radiographing operation has been performed without irradiating the X-rays (referred to as dark image), an output when radiographing operation has been performed while irradiating the X-rays with a constant intensity (hereinafter, referred to as sensitivity), and an amount of an image lag component are illustrated. The image lag component remains for an extended period of time (hereinafter, referred to as image lag amount) after artificially generating an image lag by placing an X-ray shielding substance at a portion of the X-ray sensor unit 111, and irradiating with the X-rays of great intensity.

The vertical axis of FIG. 3A indicates output values of dark image, sensitivities, and values of image lag amount beginning at the top. Further, the horizontal axis indicates a length of time that has elapsed after the bias voltage is applied on the elements. The horizontal axes of three graphs in FIG. 3A are all in the same scale, and temporal changes of three characteristics are compared on the same time axis. Given these facts, it can be seen that there is a correlation between drop of fluctuation rate of dark image output values (stability of dark image output values) and stability of sensitivities, and further there is a correlation between stability of sensitivities and generated image lag amount.

That is, as the time elapses, fluctuation of dark image output values becomes stable, sensitivities becomes more and more stable, and generation of the image lag is inhibited. It is found that, once sensitivity goes into a stable state, even when the X-ray irradiation is performed, sensitivity remains stable and a state where generation of an image lag is inhibited continues.

Figure 3B:
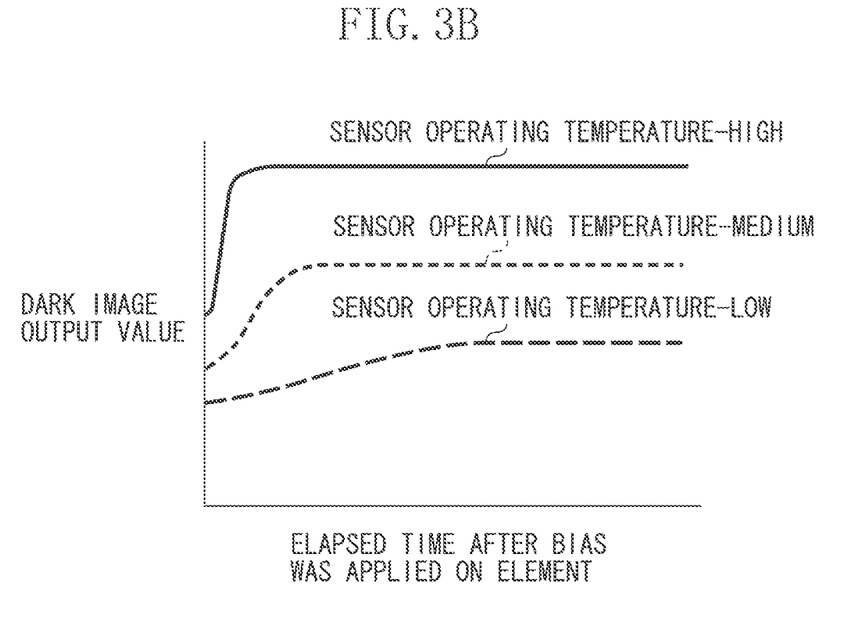

FIG. 3B illustrates an example of temporal changes of dark image output values for each temperature when operating temperatures of the X-ray sensor unit 111 are altered. The vertical axis indicates output values of the dark images, and the horizontal axis indicates a length of time that has elapsed after the bias voltage is applied on the elements. In this case, the experimental results are indicated with sensor operating temperature conceptually grouped into high/medium/low. Any of them indicates the results within a range of 5° C. to 40° C. which are ambient temperature at which the X-ray imaging apparatus according to the present exemplary embodiment generally operates.

Though not illustrated in FIG. 3B, a relationship among fluctuation of dark current output values, sensitivities, and change of image lag amounts are equivalent to the ones suggested in FIG. 3A. Given these facts, it can be seen that the higher the temperature, the earlier the dark image output values and sensitivities go into a stable state. That is, generation of the image lag can be inhibited sooner. Further, it has been found that there is a correlation between a time required before dark image output values becomes stable, and operating temperature of the X-ray sensor unit 111.

Figure 3C:
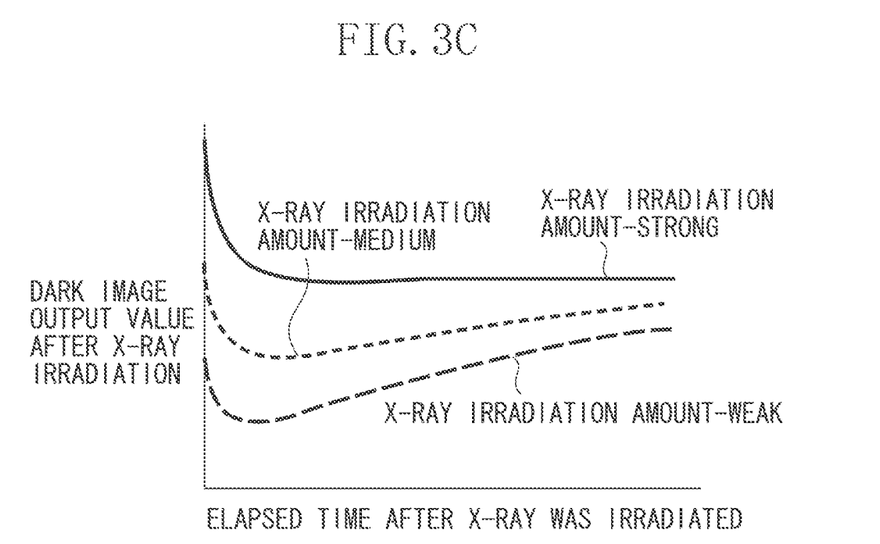

FIG. 3C illustrates an example of changes over time of output values of dark images after uniformly irradiating with X-rays above a certain amount. The irradiation with X-rays is carried out under the condition that after the bias voltage has been applied on the elements, an object body which completely shields the X-ray is not placed before sensitivity fluctuation of the X-ray sensor unit 111 occurs. The vertical axis indicates dark image output values after the X-ray irradiation, and the horizontal axis indicates elapsed times after irradiation of the X-rays is performed.

In this case, the results when irradiation amount of the X-rays has been altered are plotted. Similarly to FIG. 3B, a relationship among fluctuation of dark current output values, sensitivities, and change of the image lag amounts was equivalent to the one suggested in FIG. 3A. By performing X-ray irradiation in a sufficient amount on the X-ray sensor unit 111, it is found that the X-ray sensor unit 111 can be shifted to a state where generation of the image lag can be inhibited. It can be seen that how long a time has elapsed after the bias voltage is applied on the elements before an image lag amount is sufficiently reduced, based on the X-ray radiographing conditions such as sensor temperatures, and strong or weak amount of X-ray irradiation.

The detailed operation of the radiographing unit 11 in the present exemplary embodiment based on the above findings will be described with reference to FIG. 1.

The imaging control according to the present exemplary embodiment is based on the finding that states of the X-ray sensor unit 111 of the X-ray imaging apparatus according to the present exemplary embodiment are classified roughly into two types. Of two types of the states, a first state of the X-ray sensor unit 111 is a state where much image lag is generated, before a first predetermined time has elapsed after the bias voltage was applied on the elements. A second state of the X-ray sensor unit 111 is a state where generation of the image lag is inhibited. The second state appears when the first predetermined time has elapsed after the bias voltage is applied on the elements.

In the X-ray imaging apparatus according to the present exemplary embodiment, it is desirable to change a drive of the X-ray sensor unit 111 depending on a state of the X-ray sensor unit 111. That is, the X-ray sensor unit 111 is in the first state, in other words, a first drive is carried out when a sensor operating time after application of the bias voltage is within the first predetermined time. Then, when the X-ray sensor unit 111 is in the second state, in other words, after the first drive is performed (after X-ray radiographing), when the sensor operating time after application of the bias voltage becomes greater than the first predetermined time, it is desirable to take a second drive.

In this case, the first predetermined time is a length of elapsed time in which it is estimated that the image lag amount has been sufficiently reduced, considering the X-ray radiographing conditions such as sensor temperatures, and strong or weak amounts of the X-ray irradiation. Specifics of the first drive and second drive will be described below.

The above-described first predetermined time can be calculated using sensor operational information as parameters. The sensor operational information includes operating temperatures of the sensor unit and output values of dark images as an example. The two types of drives of the X-ray sensor unit 111 as above described are controlled by the sensor operation control unit 113 electrically connected to the X-ray sensor unit 111.

In the present exemplary embodiment, when a sensor operating time after application of the bias voltage is within the first predetermined time, the X-ray sensor unit 111 is in a state where sensitivity is not stable, and the image lag is likely to occur. As an example of the first drive, in a case where it is necessary to perform radiographing operation in such a state of the X-ray sensor unit 111, drive is performed to insert a sleep drive for each radiographing operation, thereby inhibiting generation of the image lag.

When the sensor operating time after application of the bias voltage exceeds the first predetermined time, the X-ray sensor unit 111 is in a state where sensitivity is stable and the image lag is less likely to appear. The second drive is, for example, a drive characterized by shifting to the next radiographing operation without performing the sleep drive after the radiographing operation has been finished. Since the image lag is less likely to appear on the X-ray sensor unit 111, it becomes possible to omit the sleep drive in a case where the next radiographing needs to be performed. Accordingly, inhibition of generation of the image lag is easily achieved, without extending the radiography cycle time. Control for change of two types of drives as above described is carried out by the sensor control unit 113 which has received a determination result of the sensor state determination unit 112.

The sensor state determination unit 112 includes the sensor operation information measurement unit 1121, the first predetermined time calculation unit 1122, and the determination unit 1123. At the time when the X-ray imaging apparatus according to the present exemplary embodiment performs radiographing operation, the sensor operational information measurement unit 1121 measures operational information of the X-ray sensor unit 111. In this regard, in addition to the sensor operating time after the bias application, the operational information of the X-ray sensor unit 111 may be at least one of operating temperatures of the X-ray sensor unit 111 and output values of the images acquired by the X-ray sensor unit 111 and others. As for a means for acquiring information, any publicly-known method may be used.

For example, a temperature sensor for measuring operating temperatures of the X-ray sensor unit 111 may be provided, or CPU for measuring output values of the acquired images may be provided. Subsequently, sensor operational information is input into the first predetermined time calculation unit 1122, and the first predetermined time is calculated by the function using the operational information of the sensor unit as parameters.

The calculated first predetermined time is compared with the sensor operating time after application of the bias, and determination is made by the determination unit 1123, and then is transmitted to the sensor operation control unit 113 electrically connected to the sensor state determination unit 112. The determination operation of sensor state by the sensor state determination unit 112 is repeatedly performed at a predetermined time interval and the first predetermined time is updated each time.

Figure 4:
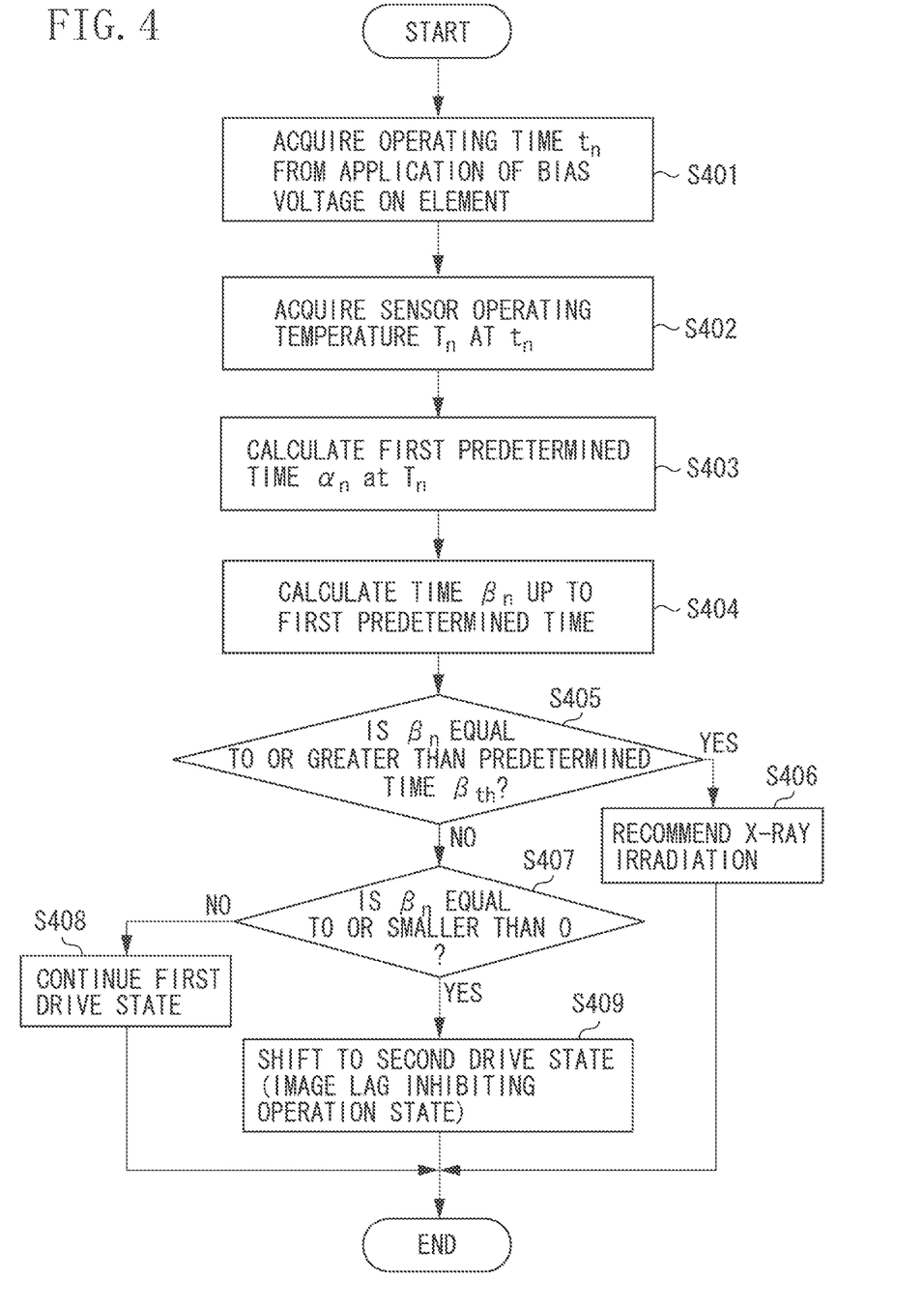
FIG. 4 is a chart illustrating a flow of the processing of a sensor state determination unit according to the first exemplary embodiment.

FIG. 4 illustrates a flow of the processing of the sensor state determination unit 112 in the present exemplary embodiment. In this case, a flow when N-th sensor state determination is performed will be described.

First, in step S401, the sensor operation information measurement unit 1121 acquires an operating time tn that has elapsed after the bias voltage is applied on the elements.

Next, in step S402, the sensor operation information measurement unit 1121 acquires an operating temperature Tn of a sensor at an operation time tn. In this case, the operations performed in steps S401 and S402 correspond to the operations in the sensor operation information measurement unit 1121 in FIG. 1.

Figure 6A:
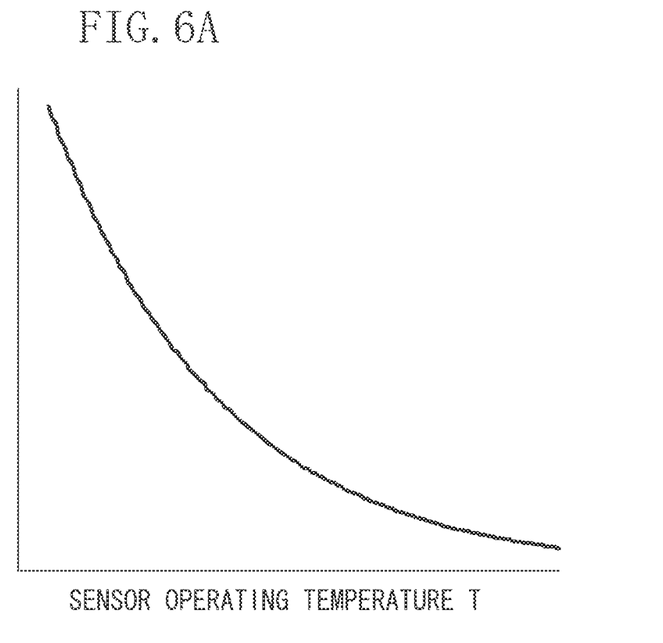
FIGS. 6A and 6B are graphs illustrating characteristic models of a sensor unit used for calculation by a first predetermined time calculation unit according to the second exemplary embodiment.

Then, in step S403, the first predetermined time calculation unit 1122 calculates a first predetermined time αn at an operating temperature Tn of the sensor. A correlation as illustrated in FIG. 6A is assumed between sensor operating temperature T and first predetermined time α, from the study results illustrated in FIG. 3 and the relationship has been mathematized as given in the equation (1). In the present exemplary embodiment, a predetermined time αn is calculated using the equation (1).

$$\alpha = A_e \tau^{-1} T \quad (1)$$

Returning to FIG. 4, the processing of the sensor state determination unit 112 will be continuously described.

In step S404, the first predetermined time calculation unit 1122 determines a time βn remaining up to the first predetermined time, from tn and αn. The time βn is calculated using the equation (2).

$$\beta_n = t_n - \alpha_n \quad (2)$$

The time βn may be displayed on the display unit 125 in the console unit 12, and may be presented to the operator as information of a time required before shifting to the second drive. The operations in steps S403 and S404 correspond to the operations of the first predetermined time calculation unit 1122 in FIG. 1.

Next, in step S405, the determination unit 1123 determines whether βn is greater than a second predetermined time βth. However, as illustrated in a mathematical model of αn in the present exemplary embodiment, when the operating temperatures of the X-ray sensor unit 111 are extremely low, as a result of the experiment, βn may become an extremely long time, which is from a practical viewpoint unsuitable.

By irradiating with the X-rays above a certain amount, when an object body that strongly shields against the X-rays is not placed, it is found through the experiment as previously illustrated, that sensitivities of the sensor unit can be made stable and an image lag is less likely to appear.

In the present exemplary embodiment, if βth is retained as a variable parameter, and βn becomes equal to or greater than βth (YES in step S405), the processing proceeds to step S406. In step S406, recommendation of the radiographing operation irradiating with the X-rays is notified to the operator, using a notification unit. Regarding a notification method to the operator, any publicly-known method may be used. For example, the operator may be notified using the display unit 125, or notification may be performed via audio or the like.

Further, as shown in the previous experiment, the X-ray sensor unit 111 may remain in a state where sensitivity is not sufficiently stable, and an image lag is likely to occur, depending on an irradiation amount of the X-rays. Therefore, output values of the radiographic images may be acquired using, for example, the sensor operational information measurement unit 1121, from the images radiographed by the operator, and it is determined whether irradiation with the X-rays in a predetermined amount has been carried out. Then the sensor unit may be shifted to the second drive. Alternatively, the processing may be caused not to proceed to step S406 by setting βth at ∞, depending on temperature characteristics of the sensor unit, or usage situation of the operator.

Then, in step S407, the determination unit 1123 determines whether βn is equal to or smaller than 0.

If βn is greater than 0 (NO in step S407), the processing proceeds to step S408, since drive of the first predetermined time needs to be performed continuously, the determination unit 1123 returns a determination result that the first drive is to continue.

On the other hand, if βn is equal to or smaller than 0 (YES in step S407), the processing proceeds to step S409. In step S409, the determination unit 1123 returns a determination result that it is possible to shift to the second drive. The operation in steps S405 to S409 corresponds to the operation of the determination unit 1123 in FIG. 1.

Through the above configurations, the operation can be easily shifted to a state where generation of the image lag can be inhibited, without adding a large-sized hardware such as a light source to the X-ray imaging apparatus, and without extending the radiography cycle time by shifting to a sleep drive for each radiographing operation.

The X-ray imaging apparatus according to the second exemplary embodiment is provided with a configuration similar to the one in the X-ray imaging apparatus according to the first exemplary embodiment illustrated in FIG. 1, but a portion of the processing of the sensor state determination unit 112 differs from the first exemplary embodiment.

Figure 5:
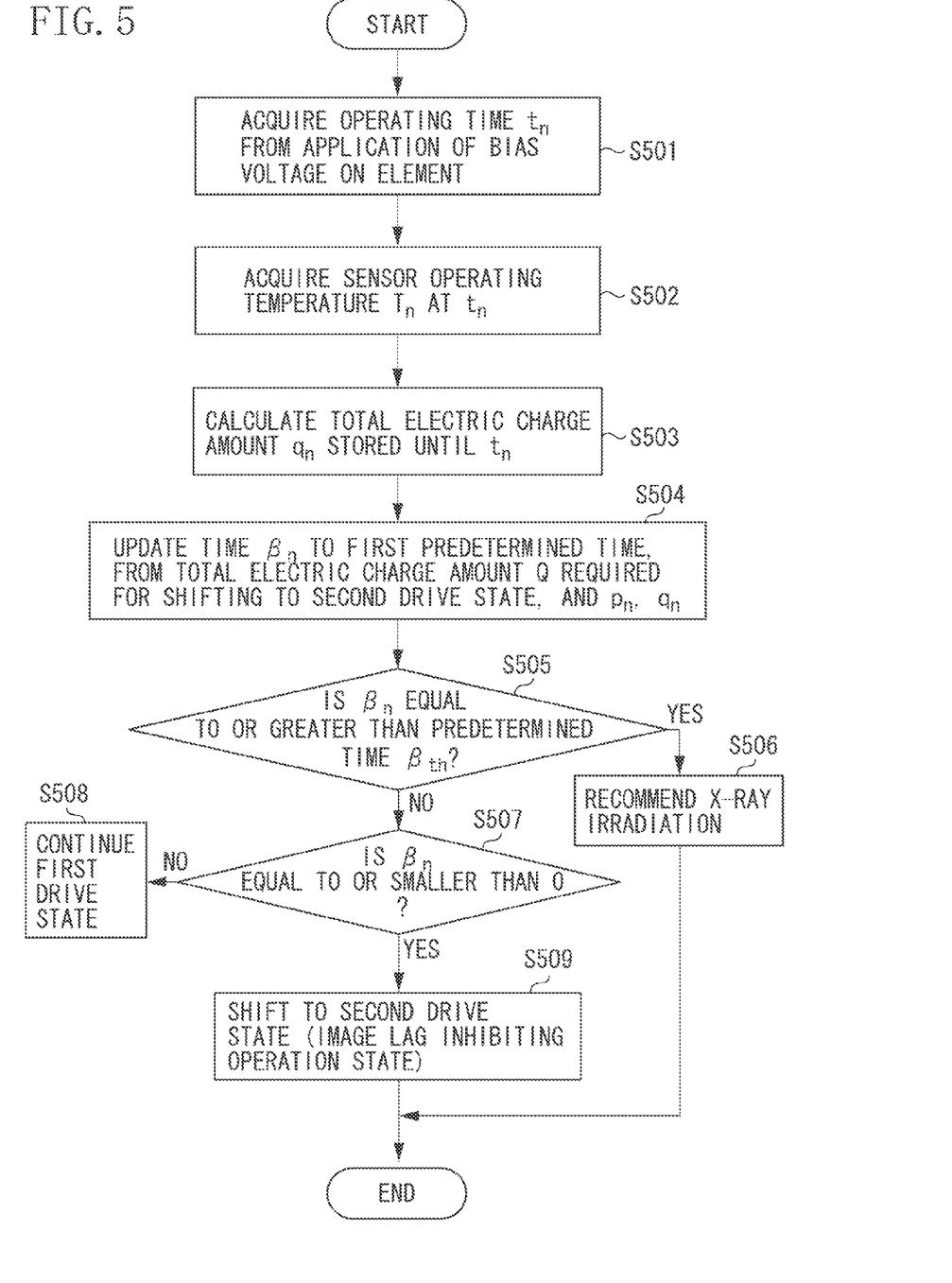
FIG. 5 is a chart illustrating a flow of the processing of a sensor state determination unit according to a second exemplary embodiment.

FIG. 5 is a chart illustrating a flow of the processing of the sensor state determination unit 112 in the present exemplary embodiment. Here, the flow in a case where N-th sensor state determination is performed will be described. In the present exemplary embodiment, only operating temperatures of the sensor unit are used as operational information of the sensor unit.

First, in step S501, the sensor state determination unit 112 acquires an operating time tn after the bias voltage is applied on the elements. Next, in step S502, the sensor state determination unit 112 acquires operating temperature Tn of the sensor unit at the operating time tn. In this case, the operations performed in steps S501 and S502 correspond to the operations of the sensor operation information measurement unit 1121 in FIG. 1.

Figure 6B:
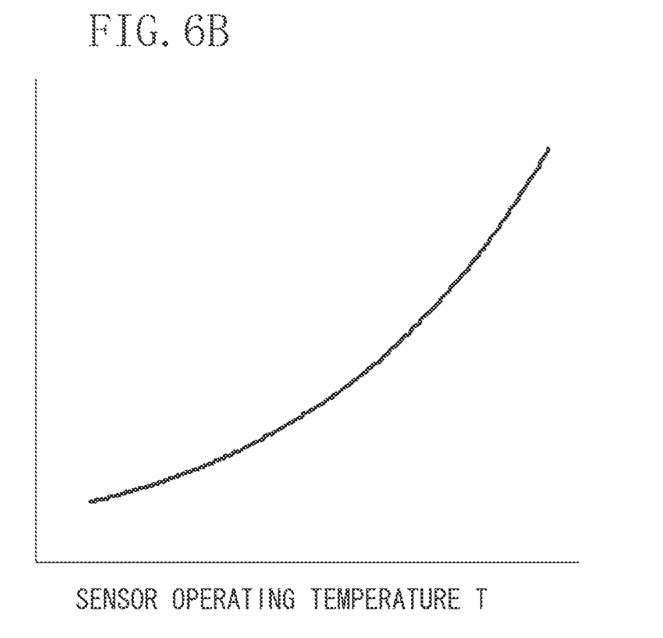

From the study results illustrated in FIG. 3, it is assumed that a total amount of electric charges which is required by the elements to shift to the second drive is determined. It is thought that dark current constantly flows through the sensor unit by continuous operation performed in the first drive. The higher operating temperature of the sensor unit, the more the amount of the dark current becomes. From this, there is a correlation as illustrated in FIG. 6B between sensor operating temperatures T and charging speeds p of electric charges, and the relationship is mathematized as given in the equation (3).

$$p = B_e^2 T \quad (3)$$

In the present exemplary embodiment, in step S503, the sensor state determination unit 112 calculates a charging speed pn of electric charge at a sensor operating temperature Tn using the equation (3), and calculates a total electric charge amount qn until a time tn, by the equation (4). In the equation (4), t0=0.

$$q_n = \sum_{i=1}^{n} p_i \times (t_i - t_{i-1}) \quad (4)$$

Next, in step S404, the first predetermined time calculation unit 1122 calculates a time βn remaining up to the first predetermined time, from a total electric charge amount qn stored after the bias voltage is applied on the elements until an operating time tn, and from a total electric charge amount Q required for shifting to the second drive, using the equation (5).

$$\beta_n = \frac{Q - q_n}{p_n} \quad (5)$$

Time βn may be displayed on the display unit 125 in the console unit 12, and presented to the operator as information of a time required for shifting to the second drive. The operations in steps S503 and S504 correspond to the operations of the first predetermined time calculation unit 1122 in FIG. 1.

Following operations in steps S505 to S509 take same procedures as those described in steps S405 to S409 in the first exemplary embodiment. The operations in steps S505 to S509 correspond to the operations of the determination unit 1123 in FIG. 1. Through the above configurations, similarly to the first exemplary embodiment, the sensor unit can be easily shifted to a state where generation of the image lag can be inhibited in the present exemplary embodiment, without adding large-sized hardware such as a light source to the X-ray imaging apparatus, and without extending an radiography cycle time. The control of the X-ray imaging apparatus described in the above-described first exemplary embodiment and second exemplary embodiment can be also realized by allowing the computer to serve as a control device by executing the predetermined computer program on a computer.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2011-272160 filed Dec. 13, 2011, which is hereby incorporated by reference herein in its entirety.

What is claimed is:

1. An X-ray imaging apparatus that performs radiographing by detecting X-rays that have transmitted through an object with an X-ray sensor, the X-ray imaging apparatus comprising:

an acquisition unit configured to acquire information related to an image lag component of the X-ray sensor; and a control unit configured to perform a drive application to alter a bias voltage on elements of the X-ray sensor by a bias power source for each radiographing operation before an amount of the image lag component becomes stable, wherein the control unit performs a radiographing operation without performing the drive application after the amount of the image lag component becomes stable.

2. The X-ray imaging apparatus according to claim 1, wherein the acquisition unit is further configured to acquire a first predetermined time based on the information related to the image lag component of the X-ray sensor, wherein the first predetermined time is a time that elapses before going into a stable state where an image lag of the X-ray sensor is inhibited, after the bias voltage is applied on the X-ray sensor.

3. The X-ray imaging apparatus according to claim 2, wherein the first predetermined time is calculated based on a function using operational information of the X-ray sensor as parameters.

4. The X-ray imaging apparatus according to claim 3, wherein operational information of the X-ray sensor includes at least one of operating temperatures of the X-ray sensor and output values of X-ray radiographic images acquired by the X-ray sensor unit.

5. The X-ray imaging apparatus according to claim 1, further comprising:

a repetition unit configured to repeat processing of the acquisition unit and processing of the control unit at a predetermined time interval.

6. The X-ray imaging apparatus according to claim 2, further comprising:

a notification unit configured to notify a recommendation of X-ray radiographing in a state where an object body which shields against X-rays is not placed, when the first predetermined time has elapsed after bias voltage is applied on the X-ray sensor after X-ray radiographing is performed by the X-ray sensor.

7. An X-ray imaging method for performing X-ray radiographing by detecting X-rays that have transmitted through an object with an X-ray sensor, the X-ray imaging method comprising:

acquiring information related to an amount of an image lag component of the X-ray sensor; and performing control of a drive application to alter a bias voltage on elements of the X-ray sensor by a bias power source for each radiographing operation before the amount of the image lag component becomes stable, wherein the performing control includes performing a radiographing operation without performing the drive application after the amount of the image lag component becomes stable.

8. A non-transitory computer readable storage medium that stores a computer program for causing a computer to serve as a control device of an X-ray imaging apparatus that performs X-ray radiographing by detecting X-rays that transmitted through an object with an X-ray sensor, the X-ray imaging apparatus comprising:

an acquisition unit configured to acquire information related to an image lag component of the X-ray sensor; and a control unit configured to perform a drive application to alter a bias voltage on elements of the X-ray sensor by a bias power source for each radiographing operation before an amount of the image lag component become stable, wherein the control unit performs radiographing operation without performing the drive application after the amount of the image lag component becomes stable.

9. The X-ray imaging apparatus according to claim 2, wherein, after the first predetermined time has elapsed, the control unit performs a drive for reducing the bias voltage to a reference voltage after a radiographing operation is altered to a drive for not reducing the bias voltage.

10. The X-ray imaging apparatus according to claim 2, wherein, after the first predetermined time has elapsed, the control unit performs a next radiographing operation without performing a sleep drive after a radiographing operation is finished.

11. The X-ray imaging apparatus according to claim 2, wherein, during the first predetermined time, the control unit performs a sleep drive each time a radiographing operation is performed.

12. The X-ray imaging apparatus according to claim 2, wherein, after the first predetermined time, the control unit performs the drive application to alter a voltage applied to an element of a signal detection unit.

13. The X-ray imaging apparatus according to claim 1, wherein the acquisition unit is further configured to acquire a change in temperature of the X-ray sensor, wherein, as the temperature of the X-ray sensor increases, the amount of the image lag component decreases and becomes stable.

* * * * *